United States Patent [19]

Aneja

[11] 4,400,553
[45] * Aug. 23, 1983

[54] RECOVERY OF BPA AND PHENOL FROM AQUEOUS EFFLUENT STREAMS

[75] Inventor: Viney P. Aneja, Schenectady, N.Y.

[73] Assignee: General Electric Company, Schenectady, N.Y.

[*] Notice: The portion of the term of this patent subsequent to Feb. 15, 2000 has been disclaimed.

[21] Appl. No.: 276,625

[22] Filed: Jun. 24, 1981

[51] Int. Cl.$^3$ ............................................. C07C 37/72
[52] U.S. Cl. ................................... 568/724; 210/806; 203/62

[58] Field of Search .............. 210/634, 659, 806, 805; 568/724, 748, 750, 749; 260/45, 95 R; 203/43, 62

[56] References Cited

U.S. PATENT DOCUMENTS 3,894,095  7/1975  Pietzsch et al. ..................... 568/748

Primary Examiner—Charles N. Hart
Assistant Examiner—Sharon T. Cohen
Attorney, Agent, or Firm—Richard J. Traverso; James C. Davis, Jr.; James Magee, Jr.

[57] ABSTRACT

A method for simultaneously extracting and recovering 2,2-bis(4-hydroxyphenyl) propane and phenol from aqueous effluent streams by liquid-liquid extraction using methyl isobutyl ketone.

12 Claims, 1 Drawing Figure

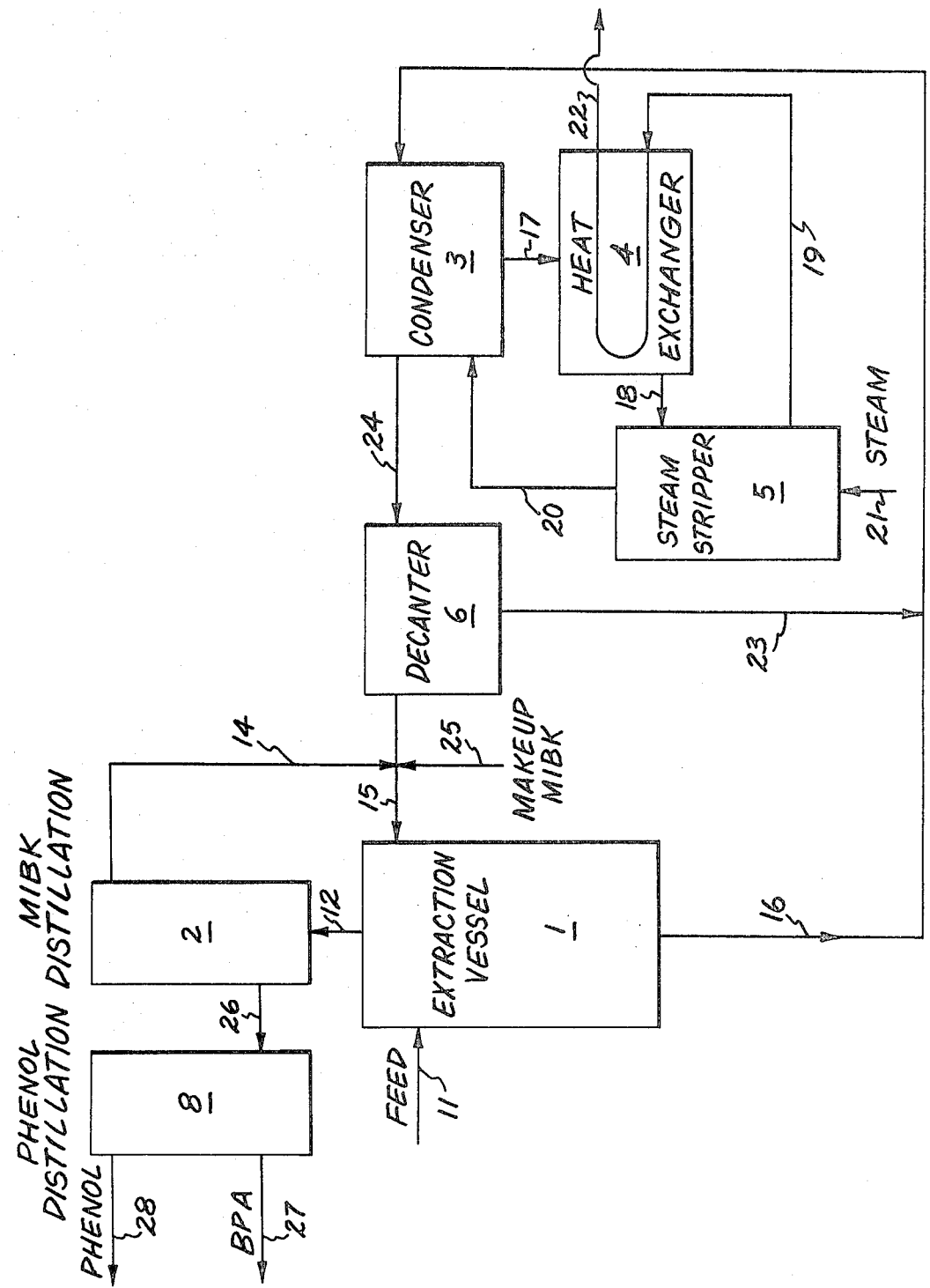

RECOVERY OF BPA AND PHENOL FROM AQUEOUS EFFLUENT STREAMS

This invention is concerned with the recovery of 2,2-bis(4-hydroxyphenyl) propane (hereinafter identified as "bisphenol A" or "BPA ") and phenol from aqueous effluent streams. More particularly the invention is directed to the simultaneous extraction and recovery of BPA and phenol from aqueous effluent streams by liquid-liquid extraction using methyl isobutyl ketone hereinafter also known as "MIBK" as the extraction solvent. The BPA and phenol are recovered in a substantially pure state for potential recycling by a subsequent distillaion step leaving MIBK which can be reused in the extraction process and water which can be disposed of without adverse environmental consequences.

BPA is commercially prepared by reacting phenol and acetone in the presence of either an acidic material such as sulfuric acid, hydrochloric acid, etc., or a cationic exchange resin. As a result of carrying out this reaction the BPA produced is accompanied by many undesirable impurities such as 2-(4-hydroxyphenyl)-2-(2-hydroxyphenyl) propane as well as other impurities including the phenol itself used in making the BPA.

Since bisphenol A is used in making polycarbonate resins by reaction of the latter with either phosgene or diphenylcarbonate, or for making epoxy resins, both resins being used extensively in commercial applications involving molding, casting, and sheet forming purposes, it is highly important that the monomeric bisphenol A used to make such resins be as pure as possible in order to avoid adverse effects on the properties of the polymers thus obtained.

The preparation of the bisphenol A by the reaction of phenol and acetone often leads to an adduct in which there is 1 mol of phenol per mol of the bisphenol-A together with any excess phenol which may have been used for reaction purposes. One method for working with this adduct to arrive at a purified bisphenol-A product is described in Luten U.S. Pat. No. 2,791,616. Accordingly to this patent the adduct obtained as a result of carrying out the initial reaction in the presence of the acidic condensation catalyst, is washed with an excess amount of water within a well defined temperature range which serves to liberate the phenol from the adduct with the result that essentially all the phenol is dissolved in the water while substantially all the bisphenol-A remains behind in the solid state. However, this process suffers from several disadvantages. Excessive amounts of water are usually required. Also, the water obtained containing the phenol, whether liberated from the adduct or the excess ammount used in carrying out the initial condensation reaction, is in the form of a solution or mixture containing both BPA and phenol. This solution or mixture requires considerable processing and expenditure of energy in order to recover the BPA and phenol so that they can be used or recycled again for reaction with acetone and so that the aqueous portion can be disposed of without having to deal with the presence of phenol, which can be toxic at very low levels, or with any other contaminants produced by the reactions.

Phenol is among the more obnoxious of the contaminants which are present in the aqueous effluent from the aqueous purification process, its taste and odor are detectable in water at concentrations of less than 4 ppm, it gives an objectionable taste to fish at 1 ppm, and it is toxic to some species of fish at concentrations as low as 0.1 ppm. In addition, when water containing phenol is chlorinated, chlorophenols are produced which give the water an objectionable taste and odor at concentrations as low as 0.001 ppm. In general, the phenol content of industrial effluents is required to be less than 1 ppm. In the absence of any U.S. government regulatory standards on BPA its content in industrial effluents is assumed to also be less than 1 ppm.

In a BPA manufacturing process which employs aqueous purification steps such as, for example, crystallization, washing, extraction, etc. substantial quantities of BPA and phenol, for example, in the order of 6%, by weight, for each are retained as major organic compounds in the aqueous stream after the aqueous purification step. These must be recovered and or disposed of in an acceptable manner. At these large concentrations there exist strong economic and environmental incentives for recovering both BPA and phenol from the aqueous effluent streams simultaneously.

Among the processes wich can be used to recover BPA and phenol from aqueous effluent streams, solvent extraction is generally preferable over steam stripping for the removal of phenols, since the phenol-water system forms a minimum boiling azeotrope at 9.2 weight % phenol. Activated carbon and resin bed adsorption have been used but the processing costs become substantial at the higher concentrations encountered here. Reverse osmosis with cellulose acetate or thin-film composite membranes is not possible. Other permeators have a limiting phenol concentration of about 5,000 ppm above which they are impractical because of their inherent design features.

The solvent most suited for the extraction of phenol from water is methyl isobutyl ketone, hereinafter also referred to as "MIBK", because of its high equilibrium distribution coefficient. Measurements of the equilibrium distribution coefficients of BPA in phenol—water and MIBK, and phenol in BPA—water and MIBK, show that direct simultaneous extraction of BPA and phenol with MIBK is effective.

The equilibrium distribution coefficients were measured for BPA between phenol plus water and MIBK, and for phenol between BPA plus water and MIBK. Batch extractions of BPA plus phenol for water by MIBK were performed in a constant temperature bath. Experiments were performed for varying temperatures less than 60° C., BPA concentrations less than 10% by weight BPA in the aqueous phase, and phenol concentrations less than 6% by weight, phenol in the aqueous phase.

The equilibrium distribution coefficient at 30° C.±1° C. was found to be $\geq 2000$ for BPA between phenol plus water and MIBK, and $\geq 60$ for phenol between BPA plus water and MIBK. At 60° C.±1° C. the equilibrium distribution coefficient was $\geq 1000$ for BPA between phenol plus water and MIBK and $\geq 40$ for phenol between BPA plus water and MIBK.

In all cases a second extraction of the aqueous phase by MIBK was also performed. Since the BPA concentration in the aqueous phase was below the detection limit of the analyzer, the equilibrium distribution coefficient for BPA in phenol plus water was undetermined but the equilibrium distribution coefficient for phenol in BPA plus water was similar to the first extraction.

The equilibrium distribution coefficient of the solvent is very important since it affects the required ratio of solvent mass flow rate to aqueous mass flow rate in continuous extraction. The high distribution coefficient of MIBK allows efficient BPA and phenol extraction at relatively low solvent ratios and allows efficient extraction with recycled MIBK which has been less thoroughly regenerated. Moreover the specific gravity of MIBK, 0.8 at 20° C., is sufficiently different from that of water, 0.989 at 20° C., so that the countercurrent flow in a continuous extraction column or settling in a mixer-settler will proceed readily.

The extraction can be carried out in a conventional extraction column using countercurrent or cocurrent exchange flows. Countercurrent extraction is the preferred method. Using this method the heavy phase (water containing BPA and phenol) enters at the top and the light phase (solvent MIBK) enters at the bottom of the column. The extract (MIBK containing BPA and phenol is sent to distillation means to separate BPA and phenol from the MIBK. The column distillate is regenerated MIBK which is recycled to the extraction column. The BPA and phenol contained as a bottoms product from the distillation are separated by further distillation in a separate tower or returned or recycled to the BPA process.

The water leaving the extraction column, as the raffinate phase, is saturated with MIBK and contains only trace quantities of BPA and phenol. This aqueous stream can be passed to a steam stripper to recover the MIBK. This MIBK is recycled back to the extraction columns for reuse. The effluent water containing trace quantities of BPA and phenol and MIBK can be further purified, if needed, by activated charcoal or an organic resin.

It has been discovered that bisphenol A and phenol can be extracted for reuse simultaneously from aqueous effluent streams using methyl isobutyl ketone as the extracting solvent. By using MIBK in a liquid-liquid extraction the aqueous effluent stream from the purification step in a BPA manufacturing process can be cleaned to a point where the aqueous portion can be disposed of in an environmentally safe manner without additional treatment. All of the chemicals; BPA, phenol, and MIBK, and water are recovered in a substantially pure state for potential recycling. The BPA, phenol and MIBK in the organic phase are separated and purified by subsequent distillation and the MIBK is optionally removed from the aqueous phase by, for example, vacuum steam stripping. There are both strong economic and strong environmental incentives for using this new process since large amounts of BPA and phenol can be recovered for recycling and in addition the resulting aqueous effluent stream from the BPA purification step can be cleaned bo both BPA and phenol to a point where it can be disposed of in a conventional manner with little or no subsequent treatment and at minimum cost.

It has also been discovered that the recovery of BPA and phenol from an aqueous effluent stream containing dissolved BPA and phenol can be accomplished by a continuous process for the simultaneous extraction and recovery of BPA and phenol using a liquid-liquid extraction with MIBK as the extraction medium. This recovery is achieved by means of a continuous process comprising the following steps:

(a) introducing an aqueous stream contaning BPA and phenol to an extraction vessel along with MIBK, (b) removing the heavy aqueous phase from the extraction vessel for further processing or disposal, (c) removing from the top of said extraction vessel an MIBK solution of BPA and phenol, and (d) recovering the BPA and phenol from said MIBK solution of BPA and phenol and recycling the MIBK to said extraction vessel.

According to the present process there may be conveniently used aqueous solutions or suspensions containing dissolved or particulate BPA and phenol. Typical aqueous concentrations can range up to 30% BPA, by weight, and up to 15% phenol, by weight and more particularly up to 10% BPA and up to 5% phenol by weight.

Solutions with low concentrations of BPA and phenol such as those obtained from the aqueous purification steps of conventional BPA manufacturing processes are particularly suitable for use in the practice of this invention. The purified or cleaned aqueous phase obtained using the process of the present invention still contains trace quantities of MIBK, phenol and BPA which may optionally be removed in the manner described previously.

The BPA and phenol recovered by distillation from the MIBK solution from the extraction vessel can be further separated from each other by distillation in separated distillation means. Using distillation to recover the BPA and phenol from the loaded solvent and to regenerate the solvent for reuse in the extraction vessel is attractive since the normal boiling point of MIBK, 119° C., is substantially lower than the very high boiling point of BPA which is 220° C., even at 4 mm Hg, and phenol 181° C. In addition, the high boiling impurities are prevented from accumulating in the recycle of MIBK steam. Such an accumulation of impurities would change the distribution coefficients and the physical properties of the MIBK extraction solvents.

The temperature at which the liquid-liquid extraction vessel is operated will be based upon economic considerations and will adventageously fall within the range of 20° C. to 80° C. and more particularly between 25° C. and 35° C. The temperature after the purification step in the manufacture of BPA is approximately 60° C. However, the solvent extraction process is more efficient at lower temperatures, e.g. approximately 30° C. The cost of cooling the aqueous effluent of the BPA purification step versus the lowered extraction efficiency at the higher temperature will dictate the extraction temperature used in individual processes.

By means of the process of the present invention using liquid-liquid extraction with MIBK solvent for simultaneously extracting BPA and phenol from an aqueous effluent stream, it is possible to recover all of the chemicals for recycling. BPA, phenol and MIBK are recovered by distillation and MIBK and water are recovered by solvent stripping means, for example, vacuum steam stripping. The presence of the present invention would lead to considerable economic benefits since large quantities of BPA and phenol could be recovered. Moreover, only one extraction solvent is being used which results in substantial reduction in solvent recovery and distillation costs when compared to a multiple solvent extraction process. The water effluent can then either be recycled in the process or discharged directly since it can substantially conform to environmental effluent standards.

The weight ratio of MIBK extractant to aqueous feed stream will depend upon the concentrations of BPA and phenol in the feed stream and the degree of recovery desired. Typical ratios can range from 0.1 parts to 2.0 parts by weight MIBK per part of aqueous feed with a preferred ratio of about 0.5 parts MIBK by weight per part of aqueous feed.

The present invention can be carried out in an apparatus as shown in the accompanying figure. An aqueous solution of BPA and phenol for example the aqueous effluent from a BPA purification process is fed via line 11 to a liquid-liquid extraction vessel for extraction with MIBK which is supplied to the extraction vessel 1 via line 15. The heavier aqueous phase from said extraction vessel from which BPA and phenol have been extracted passes via line 16 to a condenser 3 where said aqueous phase is heated and then via line 17 to a heat exchanger 4 where additional heating takes place. The heated aqueous phase from said heat exchanger then passes via line 18 to a stream stripping vessel 5 which is supplied with steam at a temperature of between 100° C. and 200° C. via line 21. Water vapor and MIBK vapor stripped from the aqueous phase are transfered via line 20 to said condensor 3 where vapors are condensed after which the condensate is passed via line 24 to a decanter 6 in which the MIBK and water phases are allowed to separate after which the MIBK is recycled to said extraction vessel 1 via line 15 and the aqueous portion is passed via line 23 back to the stripping vessel 5 for additional steam stripping. Said aqueous phase from said steam stripping vessel 5 is passed via line 19 through said heat exchanger 4 resulting in an aqueous product which is substantially free of BPA and phenol. The cleaned aqueous product may optionally be passed through an additional purification stage for example over an activated carbon adsorber or an organic resin bed which can remove additional BPA and phenol along with other contaminants. The lighter MIBK phase from the extraction vessel 1 which contains the extracted BPA and phenol is passed via line 12 to a MIBK distillation vessel 2 where MIBK is distilled from the BPA and phenol. BPA and phenol are removed via line 26 for separation by another distillation step and/or recycling or reuse and distilled MIBK is returned via line 14 for reuse for extraction in said extraction vessel. The BPA and phenol are passed via line 26 to a phenol distillation vessel 8 and finally phenol is recovered via line 28 and BPA is recovered via line 27.

In order that those skilled in the art may readily understnad how the present invention is practiced, the following example is given by way of illustration and not way of limitation.

EXAMPLE

The process of the present invention may be better understood by reference to the following description of a specific embodiment as applied to the accompanying drawings. An aqueous solution of 5% BPA and 5% phenol, by weight, is fed via line 11 to a countercurrent extraction column 1 which is maintained at about 30° C., for liquid-liquid extraction using MIBK. Equal parts by weight of MIBK and aqueous feed are used. The heavy aqueous phase from the extraction column 1 is passed via line 16 for heating through condensor 3 and heat exchanger 4 before being passed via line 18 to a steam stripping vessel 5 at one atmosphere pressure and supplied with fresh super-heated steam at about 200° C. via line 21. The steam and MIBK vapor from said steam stripping vessel 5 is passed via line 20 through condensor 3 then via line 24 to a decanter 6 where any water present in the condensate is separated. MIBK from said decanter 6 is passed via line 15 for reuse in the extraction column and the aqueous phase from said decanter 6 is passed via line 23 to line 16 for stripping. The aqueous phase from the steam stripping vessel 5 after substantially all the MIBK has been removed is passed via line 19 through the heat exchanger 4 and an aqueous product which is generally free of MIBK and phenol is removed from the heat exchanger via line 22. The light phase MIBK from the extraction vessel 1 is passed via line 12 to a MIBK distillation column 2 operating at about 120° C. and at ambient pressure. BPA and phenol are recovered as a bottom product via line 26 while MIBK is passed via line 14 for recycling to the extraction column 1. The BPA and phenol are passed via line 26 to a phenol distillation column 8 operating at about 181° C. and ambient pressure. Phenol vapor is recovered via line 28 to be condensed and reused and BPA is recovered via line 27.

Other modifications and variations of the present invention are possible in light of the above teachings. It is therefore, to be understood that changes may be made in particular embodiments described here are in the full intended scope of the invention as deifined in the appended claims.

What is claimed is:

1. A continuous process for simultaneously extracting BPA and phenol from the aqueous effluent streams produced in the aqueous purification of BPA comprising: introducing an aqueous effluent stream containing BPA and phenol to an extraction vessel along with MIBK, removing the heavy aqueous phase from said extraction vessel for further processing or disposal, removing from the top of said extraction vessel an MIBK solution of BPA and phenol, recovering the BPA and phenol solution from said MIBK solution of BPA and phenol and recycling the MIBK to said extraction vessel and, separating the BPA and phenol for recovery or recycling.

2. The process of claim 1 wherein said heavy aqueous phase from said extraction vessel is transferred to an MIBK removal apparatus where MIBK is recovered for recycling.

3. The process of claim 2 wherein said MIBK removal means is a steam stripping vessel.

4. The process of claim 1 wherein the aqueous feed stream contains up to 30% BPA, by weight, and up to 15% phenol by weight.

5. The process of claim 1 wherein the aqueous feed stream contains up to 10% BPA by weight and up to 5% phenol by weight.

6. The process of claim 1 wherein the extraction vessel is operated at between 20° C. and about 80° C.

7. The process of claim 1 wherein the extraction vessel is operated at temperature between 25° C. and 35° C.

8. The process of claim 1 wherein the extraction vessel is operated at about 30° C.

9. The process of claim 3 wherein the energy consumed in the steam stripping process is recovered by means of heat exchangers.

10. The process of claim 1 wherein BPA and phenol are separated from the MIBK solution of BPA and phenol in a distillation vessel which is operated at about 120° C. and about 1 atmosphere pressure.

11. The process of claim 1 wherein the BPA is separated from the phenol in a distillation vessel which is operated at about 181° C. and at about 1 atmosphere pressure.

12. The process of claim 1 wherein the BPA and phenol are recovered from the effluent of a BPA manufacturing process.

* * * * *